(12) United States Patent
McDevitt

(10) Patent No.: US 12,094,576 B2
(45) Date of Patent: Sep. 17, 2024

(54) SYSTEM AND METHOD FOR IMPROVED GENETIC MODIFICATIONS TO SUPPORT BENEFICIAL ADAPTATION TO UNANTICIPATED CONDITIONS AND UNINTENDED CONSEQUENCES BY UTILIZING RANDOMIZATION

(71) Applicant: John McDevitt, Clearwater, FL (US)

(72) Inventor: John McDevitt, Clearwater, FL (US)

( * ) Notice: Subject to any disclaimer, the term of this patent is extended or adjusted under 35 U.S.C. 154(b) by 844 days.

(21) Appl. No.: 17/121,675

(22) Filed: Dec. 14, 2020

(65) Prior Publication Data

US 2021/0183475 A1 Jun. 17, 2021

Related U.S. Application Data

(60) Provisional application No. 62/948,782, filed on Dec. 16, 2019.

(51) Int. Cl.
*G06N 5/04* (2023.01)
*G06N 5/02* (2023.01)
*G16B 50/20* (2019.01)

(52) U.S. Cl.
CPC ............... *G16B 50/20* (2019.02); *G06N 5/02* (2013.01); *G06N 5/04* (2013.01)

(58) Field of Classification Search
CPC .......... G16B 50/20; G16B 50/30; G06N 5/02; G06N 5/04; G06N 20/00; G06N 5/046
See application file for complete search history.

(56) References Cited

U.S. PATENT DOCUMENTS

| 8,954,337 | B2* | 2/2015 | Tebbs ..................... | G16B 45/00 705/2 |
| 2004/0142371 | A1* | 7/2004 | Milosavljevic ........ | G16B 25/10 435/6.12 |
| 2010/0138204 | A1* | 6/2010 | Eoff ....................... | G16H 50/20 703/11 |
| 2010/0305929 | A1* | 12/2010 | Andersen ................ | G16B 5/00 703/11 |
| 2013/0046994 | A1* | 2/2013 | Shaw ..................... | H04L 9/0866 713/189 |
| 2015/0169822 | A1* | 6/2015 | Kitano ................... | G16B 35/00 506/18 |
| 2015/0317432 | A1* | 11/2015 | Silver .................... | G16B 20/20 702/19 |

(Continued)

*Primary Examiner* — Hien L Duong

(57) ABSTRACT

A system and method that provides a rule-based process utilizing a managed randomization procedure for the purpose of improved genetic modification. The system includes a database that stores specific genetic sequences. Additionally, included is a genetic sequence rules engine that generates a sequence of approved genetic content based on genetic characteristics rules and a predictive rules engine that produces genetic sequence content selection characteristics based on biologic goal(s). A randomization engine is applied to the planned genetic sequence to build a set of alternate genetic sequences. Furthermore, by applying the generated genetic characteristics rules to the list of approved genetic elements to select genetic edits, such that the targeted genetic characteristics are optimized, and negative characteristics are minimized in accordance with the goal(s) of the process. This process may occur in a computer test environment, a controlled laboratory environment, and/or the natural environment.

4 Claims, 3 Drawing Sheets

(56) References Cited

U.S. PATENT DOCUMENTS

| | | | | |
|---|---|---|---|---|
| 2016/0048564 | A1* | 2/2016 | Bassett, Jr. | G16B 50/00 |
| | | | | 715/230 |
| 2016/0321935 | A1* | 11/2016 | Mohler | G09B 5/08 |
| 2018/0121601 | A1* | 5/2018 | Hahm | G16B 50/40 |
| 2018/0285520 | A1* | 10/2018 | Butruille | G16B 20/20 |
| 2019/0100809 | A1* | 4/2019 | Kennedy | G16H 50/20 |
| 2020/0102571 | A1* | 4/2020 | Tschaplinski | C07K 14/415 |
| 2021/0151123 | A1* | 5/2021 | Araya | G06F 18/24133 |
| 2021/0183475 | A1* | 6/2021 | McDevitt | G16B 50/20 |

* cited by examiner

SYSTEM AND METHOD FOR IMPROVED GENETIC MODIFICATIONS TO SUPPORT BENEFICIAL ADAPTATION TO UNANTICIPATED CONDITIONS AND UNINTENDED CONSEQUENCES BY UTILIZING RANDOMIZATION

CROSS REFERENCE TO RELATED APPLICATION

This application claims priority to U.S. Provisional Application No. 62/948,782, entitled System and Method for Improved Genetic Modifications to Support Beneficial Adaptation to Unanticipated Conditions and Unintended Consequences by Utilizing Randomization, filed on Dec. 16, 2019 the contents of which are incorporated herein by reference into the present application.

BACKGROUND OF THE INVENTION

A wide variety of approaches to genetic modification, especially for subsequent genotypes, phenotypes, exhibitions, or manifestations of certain characteristics in future generations, have been utilized for centuries. The complexity and specificity of genetic modification approaches have increased over time. Historical methods including but not limited to (individually or in combination); Selective Breading, Mutagenesis, Polyploidy, Protoplast Fusion, Transgenesis, and Genome Editing have provided means of genome manipulation that have resulted in genetic structures which met the goal(s) of the genetic modification or editing process(es). The role of specific sections of some organisms' DNA have become understood, where some specific genetic base pairs are known to control a given trait, but the roles of the vast majority are not fully understood (for example only a fraction of the approximately three billion base pairs of human DNA are fully understood).

Moreover, recent developments in genetic editing such as clustered regularly interspaced short palindromic repeats (CRISPR) and especially CRISPR associated protein 9 (CRISPR/Cas9 or CRISPR-Cas9), CRISPR Prime and other CRISPR related approaches including but not limited to; Cas3, Cas5, Cas8a, Cas8b, Cas8c, Cas9, Cas10, Cas10d, Cas12, Cas12a, Cas12b, Cas12c, Cas12d, Cas12e, Cas12f, Cas12g, Cas12h, Cas12i, Cas12k, Cas13, Cas13a, Cas13b, Cas13c, Cas13d, Cmr5, Cse1, Cse2, Csf1, Csm2, Csn2, Csn4, Csx10, Csx11, Csy1, Csy2, Csy3, GSU0054, C2c4, C2c8, C2c9, or other related approaches (collectively referred to as CRISPR herein) have been utilized to adjust the entire genome or any subset of the genome (and related phenotype and or genotype) of a given set of genetic content or organism and potentially the progeny of the genetically edited genetic content or organism. These genetic modifications are generally for the purpose of maximizing or minimizing a particular trait or set of traits (or characteristic(s)) for some benefit, however, given the very high complexities and intricacy of genetics in general (e.g., interdependent systems), and the added complexities and intricacy of the external environment (e.g., multiple interconnected independent systems) in which the organism exists, final results of the modification in the genetic code and/or the subsequent generations of the genetic code may no longer have the desired trait (or characteristic(s)) and/or the originally desired trait (or characteristic(s) may actually be found to be detrimental to the genetic code, organism, or the broader environment. Furthermore, there is the high likelihood of other unintended results stemming from the modifications.

While these genetic editing tools are extremely powerful the changes they can make are introduced very quickly and at specific locations in the genetic sequence at the direction of the editor, not the result of evolution and/or adaptation over time. Given the complexity of the internal genetic systems and the compounding complexity of the external environment, the risk of failing to achieve the goal(s) of the genetic editing is extremely high. Given this approach, if the goal(s) are not exactly achieved then the entire editing process is a failure.

This type of failure to reach the goal(s) can be very costly in terms of time, resources, expenses, and often more importantly in terms of the genetic content, organism(s) themselves, and their later generations—especially if they are sentient, rare, or broadly impacting organisms. Furthermore, the editing may result in unintended genetic consequences that may create expensive mistakes—possibly even introducing detrimental genetic structures into the broader environment. The challenge with such precise and specific genetic editing is that it does not provide any flexibility for the resulting genetic structure to succeed when there are mistakes in the editing (including but not limited to, misplaced cuts, improper removals of genetic content, improper additions of genetic content, etc.), as well as unforeseen internal or external challenges that cause the resulting genetic content to not meet the intended goal(s). A more robust solution is required to ensure longer term success of the genetically edited content and if appropriate its progeny, as well as the related resources.

SUMMARY OF THE INVENTION

Accordingly, there is a need in the industry for a method and system that identifies and structures modifications of genetic material to achieve a given set of goal(s). Generally, goal(s) are the maximizing or minimizing a particular trait or set of traits for some benefit. Due to the fact that the role of much genetic content is not completely understood, the potential unforeseen impact of genetic edits, the very precise nature of genetic edits, the complexity and ephemerality of the genetic content or organisms, as well as, their internal and external environments an intended managed randomness can be introduced to the genetic editing process to ensure a robust set of edits and a higher likelihood of achieving the given goal(s) in as many environments (internal and external), for as long as desired. This type of solution would save a great deal of time and resources in genetic editing—resulting in far improved results. Given the very nature of genetic editing, timely understanding of the results of any given edit is critical—saving even a portion of the time that makes up a generation of the genetic material or of an organism would result in a minimum of an arithmetic savings of time and if multiple simultaneous edits are occurring the time savings could be exponential. While time is often the most critical element in such matters, there would also be a material savings in resources (editors, facilities, biological resources, machines, etc.), also a savings in the initial genetic content and organisms themselves, any resulting generations, and potentially the broader ecosystem. Each of these savings individually or in combination would result in a significant expense savings.

Accordingly, there is a need in the industry for a method and system that improves the results of genetic editing to support beneficial adaptation to unanticipated conditions and unintended consequences. The system and method disclosed herein provides a rule based randomized genetic editing system. The term genetic editing ("Genetic Editing" or "GE") as used herein may include, but is not limited to, the manipulation (the adding, and/or removing, and/or changing/modifying/moving/substituting by any means, including CRISPR) any portion of genetic content including the gene bases—adenine, cytosine, guanine, and thymine ("A", "C", "G", and "T") (or their analogues), genes, or alleles, individually, in groups (including RNA, DNA, and any analogous material), up to and including the entire genome. These Genetic Edits may be temporary or permanent in a given organism or later generations of the organism (or cross-bread later generations) where the resulting traits (or characteristic(s)) may be visible, invisible, recessive, dominant, exhibited in the genotype, and or phenotype of the organism and or resulting generations (of the genetic material or the organism). Additionally, these Genetic Edits may be done to DNA, RNA, or any analogous genetic structure (or portion of genetic structure) in whole or in part. These Genetic Edits may occur completely once (in a single or in multiple organisms, to all the genetic material in an organism, an individual piece of genetic material, or a set/subset of genetic material), or in stages over time (in one piece of genetic material, a set/subset of genetic material, all of an organism's genetic material), or at once or in stages over time in multiple organisms (in one piece of genetic material, a set/subset of genetic material, all of an organism's genetic material) and this could include over multiple generations of genetic material in a given organism, multiple generations of an organism, or a population of organisms. The Genetic Editing process may be done in parallel, in sequence or in combination across any of the aforementioned groupings. All the genetic material that is capable of being involved in GE (directly or indirectly) (physically, digitally, or in combination) may be referred to as Genetic Content (or "GC"). Additionally, the GC may be actual physical material, digital virtual material, or a combination of the two. And similarly, the GE may be done in the physical world, the digital virtual world, or a combination of the two. The mechanisms utilized to do the GE to the GC will be described in greater detail below.

The system and method disclosed herein has a variety of rule sets but collectively these rules sets are used in a coordinated way, taking into consideration constraints, to arrive at desired final outcomes manifested in how GE GC meets goal(s), and these goal(s) may not just be individual genetic structure, or organism performance, but how that genetic structure meets the goal(s) of the broader ecosystem in which it exists. Please note the term "sets" used generically herein and may mean any collection of a given thing (including the null set (an empty set), a singular set (a set with a single component), or multiple set (a set with multiple components)). This system and method is not limited only to the specific gene bases, but rather also, the broader impact of the GE to sets of gene bases (including those that may not have been specifically edited). Furthermore, the system and method is not just around one organism's strand(s) of GC (RNA and/or DNA and/or analogous structure), but rather the complex interaction and possible unintended consequences of GE to one or more than one sets of GC in one or more than one organism (e.g., modifications may include changes to RNA and/or DNA in one organism, as well as, changes to multiple organisms—that could be genetically related and/or unrelated organisms in an ecosystem). These types of inter-related systems are extraordinarily complex, and any changes introduced into ecosystems often result in unforeseen and unintended results.

The term rule(s) is used generically (often in the simplest form being If-Then statements) and may include, amongst other things, one, some, or all set(s) of rules including, amongst others, ecosystem rules around processes and results (e.g., inclusions, exclusions, optimization, maximization, minimization, commercial rules, business rules, legal rules, ethical rules, etc.), genetic content rules (e.g., inclusions, exclusions, complexities, similarities to other organisms, etc.), predictive rules (e.g., math rules, modeling rules, quantitative rules, qualitative rules, etc.), genetic structure rules (e.g., biological rules, structural rules, bio-chemical rules, physical rules/limitations, etc.), and randomization rules. All of these rules may be individualized or grouped, they may be preferences, relative requirements or absolute requirements, they may be interdependent partially or wholly, they may be hierarchical in nature, they may be sequential, they may occur in parallel, or a combination of any of these. Furthermore, these rules may act as logical engines that may organize, prioritize, include, exclude, change the likelihood, etc. of a given individual genetic edit (or set of a genetic edits) to be used. The rules may be set by an individual, group, a system, a computer, another set of rules, hierarchical rule sets, or a combination of any of these. The rules may be pre-established, dynamically established, established in steps, or a combination of any of these. The results of the genetic edits may be evaluated by a user of the system. Please note the terms; "results", "product", "outcome", may be used interchangeably, generically, and could mean the results (the exhibited, hidden, dominant, recessive, latent, visible, invisible, temporary, permanent, multigenerational, or inter-organism manifestations in the organism, multi-organism, the entire ecosystem, and/or any subset). Similarly, "reviewer", "user", "viewer", "evaluator", and "consumer" are used interchangeably, generically, and could mean any reviewer of the results of the genetic edits and the user could be a human individual, a group of humans, an organism or organisms, a computer system, or set of systems. Additionally, the term "review" is used generically and can mean any method of consumption, review, analysis, etc. by a user of the genetic edit results.

The set of rules are applied to starting genetic material, which may include among other things a set of gene bases (A, C, G, & T) (partial or complete with original or substituted organic material), a full or partial piece of GC, an organism, reproductive elements of an organism, and a collection of organisms. Furthermore, genetic material may be removed, added, supplemented, created, altered, or moved (individually or in combination) in relation to the starting genetic material by means of genetic editing tools such as CRISPR or other similar methods following standard and emerging industry processes. Then a set of randomization approaches to the proposed genetic structure are applied within a set of parameters (and genetic content) to arrive at the final genetic structure.

The results of the final genetic structure of the GC—including any or all of the genome itself, the organism, the progeny of the organism, groups of organisms, and the ecosystem—are reviewed and analyzed to evaluate how the final results compare to the initial goal(s). These evaluations may occur at one or more points in time (taking into consideration delayed impacts) to measure robustness and success of the GE. It should be noted that this system and method disclosed herein has an inherent feedback loop and the entire process or any subset(s) of the process may happen once or multiple times and may occur in an iterative way where the same GC, organism, related organisms, and/or groups of organisms may be edited multiple times (in parallel or in series) over time where the results may be reviewed and then depending on the nature of the results additional cycles through the system may occur. These processes may occur once or multiple time in rapid or delayed succession (also in parallel, in series, or a combination of these).

All of the processes of the disclosed system and method may occur in the physical world or virtually in a digital environment or a combination of the two. Furthermore, the disclosed system and method may be structured of at least one (or more) database, and at least one (or more) processor (may be described as a server) configured to be communicatively coupled and configured to act in a coordinated way. By means of example but not limitations the at least one genetic content database may store actual physical organic material, or alternatively it may store data that describes organic material, or it may store both physical and digital material. The at least one (or more) database and the at least one (or more) processor may be physically located together or apart. The at least one processor(s) have resident software (and additional software may be added over time) to enable the at least one processor(s) to perform the disclosed activities including but not limited to acting as rules engines. The digital environment (especially the modeling of the potential genetic structure, the randomization process, the finalized genetic structure, and the evaluation of the results of the genetic edit, the impact of it, and the iterative feedback process) may utilize traditional classical computing, quantum computing, and a combination of the two. These computing processes may also use artificial intelligence/machine learning (AI/ML) systematic approaches to increase the efficiency and performance of the system, improving quality while reducing time and other system resources.

The system disclosed herein is a system for selecting and editing exiting genetic content in order to achieve a set of goals while minimizing resource consumption, the system comprises: at least one electronic database configured to store at least one set of existing genetic content configured to be edited by means of the addition of at least one set of new genetic content stored in at least one electronic database and/or the removal of at least one set of genetic content (and or moving or re-positioning of genetic content), the identity of which is stored in at least one electronic database; at least one processor with software instructions stored thereon that, when executed by the at least one processor, configure the at least one processor to execute: a base genetic structure rules engine configured to generate at least one approved genetic structure characteristic based at least on one ecosystem rule; including a predictive rules engine configured to generate at least one genetic structure characteristic based on at least one other historical genetic editing result(s), a randomization of genetic structure by means of at least one randomization of genetic structure rules engine configured to apply randomization rules to the genetic structure rule set to randomize the selected at least one set of genetic structures. Also, a base genetic structure engine configured to generate a set of edited genetic content by at least one of; adding at least one set of new genetic content; removing at least one set of existing genetic content—to or from the at least one set of existing genetic content such that the process resource consumption is minimized by creating the edited genetic content that is most likely in compliance with the ecosystem rules and goals. Furthermore, at least one processor configured to enable the edited genetic content to exhibit the results of the editing, wherein the results of the editing are evaluated as to their relative achievement of the ecosystem rules and goals, wherein at least one predictive rules engine is further configured to: receive updates (periodically and or continuously based on pull and or push commands) related to at least one other historical result and at least one edited genetic structure result, and correlate the at least one result of the genetic edit with the at least one exhibited characteristic and compare the at least one result with the ecosystem rules and goal(s).

Furthermore, the disclosed system includes a genetic structure rule set engine that is further configured to calculate the set of approved genetic structure(s) based on at least one other historical result of genetic editing. The disclosed system also has at least one predictive rules engine that is configured to calculate at least one "best guess" genetic structure based on at least one set of evaluated results and automatically calculate the at least a second "best guess" genetic content structure characteristic based on at least a second set of evaluated results. Furthermore, the disclosed system has at least one predictive rules engine that is further configured to receive evaluated results data related to at least a first genetic content edit and auto-calculate at least a second "best guess" genetic structure characteristic in response to a more than first genetic content edit. Also, the disclosed system has at least one genetic structure rule set engine that is configured to calculate a weighing for the selected and randomized subset(s) of the plurality of possible genetic structures, and the probability of at least one finalized genetic structure is created in part based on the calculated weighing.

The method disclosed herein for selecting and editing exiting genetic content in order to achieve a set of goals while minimizing resource consumption includes; storing in at least one electronic database configured to store at least one set of existing genetic content configured to be edited by means of the addition of at least one set of new genetic content stored in at least one electronic database and/or the removal of at least one set of genetic content, the identity of which is stored in at least one electronic database. Also, generating by at least one processor with software instructions stored thereon that, when executed by the at least one processor, configure the at least one processor to execute: generating by at least one base genetic structure rules engine configured to generate at least one approved genetic structure characteristic based at least on one ecosystem rule; applying a predictive rules engine configured to generate at least one genetic structure characteristic based on at least one other historical genetic editing result(s); applying a randomization of genetic structure by means of at least one randomization of genetic structure rules engine configured to apply randomization rules to the genetic structure rule set to randomize the selected at least one set of genetic structures; and applying a base genetic structure engine configured to generate a set of edited genetic content. This may be achieved by at least one of; adding at least one set of new genetic content or removing at least one set of existing genetic content to or from the at least one set of existing genetic content (or also moving a set of genetic content), such that the process resource consumption is minimized by creating the edited genetic content that is most likely in compliance with the ecosystem rules and goals. The disclosed method also may utilize at least one processor configured to enable the edited genetic content to exhibit the results of the editing, wherein the results of the editing are evaluated as to their relative achievement of the ecosystem rules and goals. Also, where at least one predictive rules engine is further configured to: receive updates (periodically and or continuously based on pull and or push commands) related to at least one other historical result and at least one edited genetic structure result and correlate the at least one result of the genetic edit with the at least one exhibited characteristic and compare the at least one result with the ecosystem rules and goal(s).

The disclosed method includes the genetic structure rule set engine which may be configured to generate the set of approved genetic structure(s) based on at least one other historical result of genetic editing. Also, the disclosed method may include at least one predictive rules engine that may be configured to generate at least one "best guess" genetic structure based on at least one set of evaluated results and also automatically generate at least a second "best guess" genetic content structure characteristic based on at least a second set of evaluated results. Furthermore, the disclosed method may include at least one predictive rules engine configured to receive evaluated results data related to at least a first genetic content edit and may also auto-generate at least a second "best guess" genetic structure characteristic in response to a more than first genetic content edit. Additionally, the disclosed method may include at least one genetic structure rule set engine that may be configured to determine a weighing for the selected and randomized subset(s) of the plurality of possible genetic structures, where the probability of at least one finalized genetic structure is created in part based on the determined weighing.

DETAILED DESCRIPTION

The following detailed description outlines possible embodiments of the proposed system and method disclosed herein for exemplary purposes. The system and method disclosed are in no way meant to be limited to any specific combination of hardware and software. As will be described below, the system and method disclosed herein relate to the GE of GC to achieve a set of goal(s) in accordance with a set of rule(s). It should be appreciated that each of the components in the figures below are illustrated as simple block diagrams, but include the requisite biological, mechanical, physical, digital, hardware, and software components needed to perform the specified functions as would be appreciated by one skilled in the art. For example, one or more of the components described below can include one or more databases, one or more computer processor units (CPUs) configured to execute software programs stored on electronic memory in order to execute the algorithms disclosed herein, these databases and CPUs may be located together or apart, physical, or virtual, and may be classical, quantum, or a combination of the two types of computer processors. In general, the term computer can refer to classical computing, quantum computing, artificial intelligence, machine learning, and any combination or subset of these, and these approaches may be applied sequentially or in parallel (or a combination of these) and amongst other things may act as rules engine in performing the various tasks herein.

Figure 1:
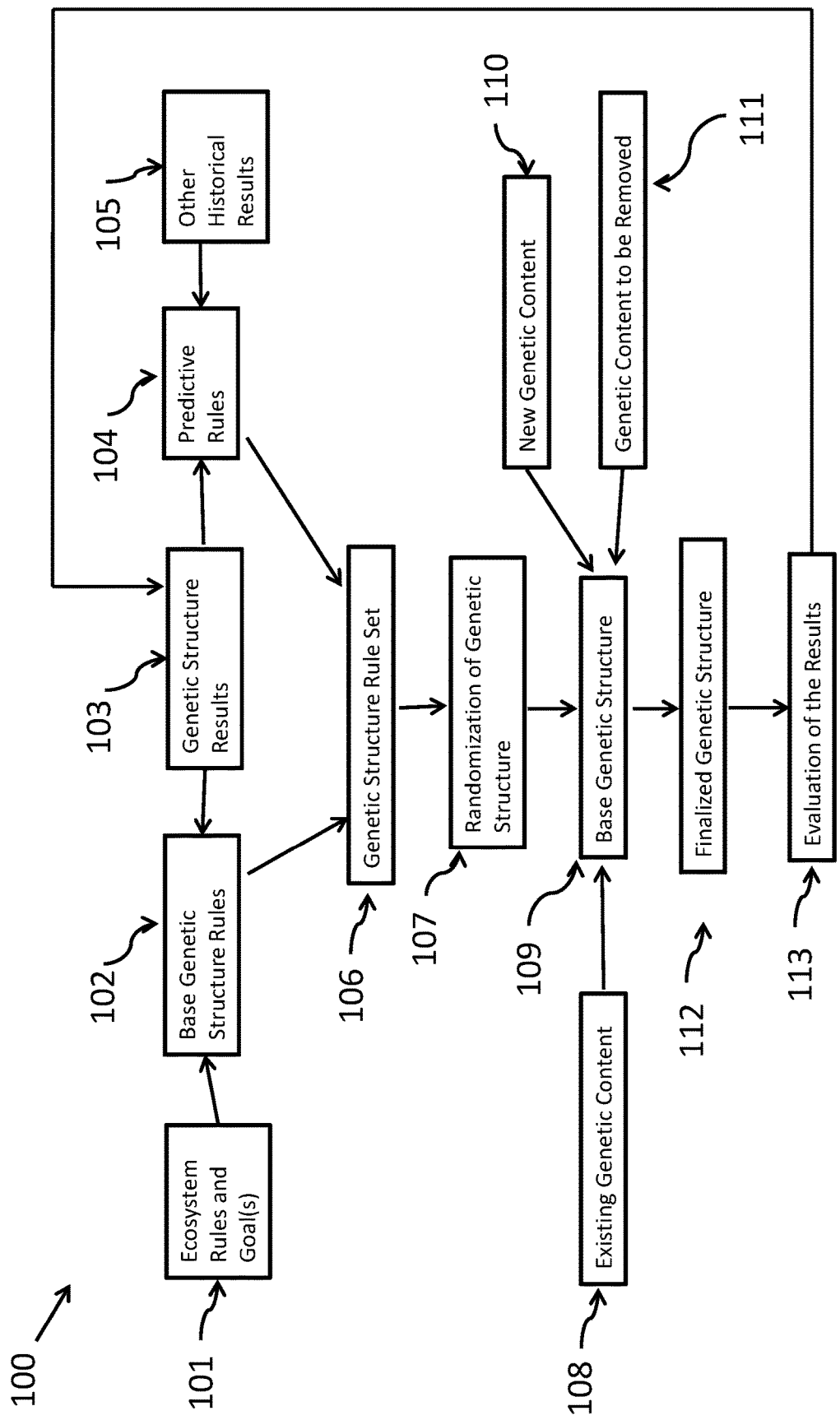
FIG. 1 illustrates a block diagram of a system for creating and evaluating modified genetic content in accordance with an exemplary embodiment.

For example, but not limitation, FIG. 1 is a basic explanatory example of the modifying of genetic content to make a more robust set of GC that meets the goal(s) of the described system and method. In this case the system can be considered a Genetic Content Modification System (100). This system (GCMS) is capable of acquiring GC, modifying GC, editing GC, combining GC, evaluating edited GC, and then depending on the results, revise, and re-process the GC multiple times. The specific components and functionality of the GCMS will be described in more detail below. It should be noted that each of the following elements may be performed systematically and automatically with or without user intervention, or each may also be performed with a user over-ride. Additionally, the rules of this system (100) may be pre-set or may be dynamically adapted in real-time/near real-time (continuously or periodically), and the adaptations may be based on the information that is available at that time, and also as additional information becomes available the rules may be further dynamically (continuously or periodically) adapted. These changes may be based on either or a combination of user/AI/ML input and will be described in more detail below.

According to the exemplary example, the GCMS (100) has a set of Ecosystem Rules and Goal(s) (101), which may be a limited or extensive set of rules that can be used to set requirements or limitations on the GC that may be utilized in the GCMS and/or the results of the GE. The Ecosystem Rules and Goal(s) (101) may be stored in electronic memory, a rules database, or the like, for example. Moreover, these Ecosystem Rules may cover a wide variety of things including or excluding, by way of example, but not limitation: GC inclusions, exclusions, placements, prioritization, weighting based on; GC source, GC type, viability, intellectual property restrictions or requirements, licenses, date of creation, geographic source, maximum GC set length, minimum GC set length, maximum number of GC samples, minimum number of GC samples, quality of GC, business rules, legal requirements, ethical considerations, individualized or grouped preferences, and the like, either individually or as a set and these can each be prioritized. While discussed further below, there may be different GC modification rule sets based on elements, including but not limited to; source of the GC, impact of the GC, ethics, legal considerations, business considerations, impacts on future generations, impact on the broader ecosystem, and the like. The different variable characteristics that drive the selection of the GC may be weighted in any proportion as deemed appropriate such that GC items may be specifically included, excluded, prioritized, and/or given a likelihood of being included in a final modified GC. Cumulatively, the Ecosystem Rules and Goal(s) (101) provide the definition of what GC is qualified to be included in the Base Genetic Structure (109) and even considered to be included in the Finalized Genetic Structure (112). Furthermore, Ecosystem Rules and Goal(s) (101) is where the goal(s) of the process are set and these goal(s) (and the relative achievement of these goal(s)) influence how the rest of the process works.

The Ecosystem Rules and Goal(s) (101) provides the first set of information that helps to create the Base Genetic Structure Rules (102). The second set of information that also helps to create the Base Genetic Structure Rules (102) is Genetic Structure Results (103). The Genetic Structure Results (103) are an interpretation of the results of the GCMS (100) system. This review may be done by a computer, by a human(s), or a combination of both (e.g., user(s)). Please note that for an entirely new genetic modification process there may be no Genetic Structure Results, or there may be results from other related genetic modifications. Alternatively, if the example genetic modification is an iterative process there may be information related to the earlier cycles and/or other related modification processes. This information may be dynamically altered in real time (or near real time) or periodically as additional information is collected especially as additional iterations of the same or similar genetic modification(s) processes are reviewed. This information can cover a wide variety of topics including but not limited to the performance of the genetic modification relative to the broader goal(s). These are often dealing with exclusions or inclusions of various genetic structures (and the manifestations of them). The combination of the Ecosystem Rules and Goal(s) (101) and the Genetic Structure Results (103) form the Base Genetic Structure Rules (102). This set of Base Genetic Structure Rules (102) provides the starting point for a structure of GC that satisfies all the broader rules as well as the results from earlier cycles of the process (if any).

The Genetic Structure Results (103) provides the first set of information that helps to create the Predictive Rule (104) sets. The second set of information that also helps to create the Predictive Rules (104) is Other Historical Results (105). As discussed earlier, as results of the performance of the given genetic modification process(es) (if any) are created they are assembled continuously or periodically (including in real time or near real time) and collected in the Genetic Structure Results (103). Similarly results of the performance of any other genetic modification processes (if any) are created they are assembled continuously or periodically (including in real time or near real time) and collected in the Other Historical Results (105). It should be noted that these results sets can be immediate results, short term results, and/or long-term results (individually or in combination) and their relationship to the goal(s). This result information helps to take into consideration the impact of complex interdependent systems and otherwise unanticipated circumstances on the results of genetic modifications. The Predictive Rules (104) may combine these two data sets that provide a broad collection of information about the results of various genetic structures. This collection of information and calculations by the Predictive Rules (104) may act as a decision engine and can provide the basis for creating high quality predictions of the results of various genetic structures and help to identify sets of structures that are most likely to provide the desired results.

The Original Genetic Structure Rules (102) and the Predictive Rules (104) combine to create the Genetic Structure Rule Set (106). This set combines the goal(s) of the process and predictive information to calculate the genetic structures that most likely provide results to achieve those goal(s). This is the theoretical "best guess" genetic structure or structures. It should be noted that due to the fact that a great deal of the genetic structure of many organisms are not well understood the "best guess" may just be that—though through an iterative process with multiple cycles (in series or parallel) the quality of these genetic structures continue to improve. Furthermore, these "best guesses" may be created, reviewed, and or altered by one or more humans or computers, or any combination of these (e.g., user(s)).

Due to the complexity of the interrelated systems, unanticipated conditions and unintended results, the results, even from well informed "best guess" genetic structures may not successfully achieve the goal(s) of the process. To improve results and likelihood of successfully achieving the goal(s) a randomization process is applied to the Genetic Structure Rule Set (106) information. The randomization and randomization rules created by the Randomization of Genetic Structure (107) process can be applied. A variety of standard randomization approaches may be used, including but not limited to any one of the following techniques (or a combination of multiple techniques, with or without element repetition, and with or without sequencing); simple, replacement, block, permuted block, biased coin, minimization, stratified, covariate adaptive, and response adaptive. In application and testing of the various randomization techniques subject blinding (and or experimenter/subject double-blinding) may be used. This variety of presentations that is achieved through randomization provides additional observations related to the performance of different GE in different sequences and/or different sets of GC that may be used to further improve optimization analyses and results. For the purpose of illustration, the "best guess" genetic structure is like a single dart thrown at a bull's eye while Randomization of Genetic Structure (107) process creates a set of genetic structures (e.g., multiple darts) with a higher likelihood of actually hitting the bull's eye than the original "best guess". Additionally, the randomization may also have rules and limitations that amongst other things, the number of GE results, give prioritization or a higher likelihood (weighting) of various GEs with specific characteristics based on rules similar to the Ecosystem Rules (101) and the Base Genetic Structure Rules (102). The weighting(s) may be established by an individual or by a system (e.g., user(s)) and take into consideration, by way of example, but not limitation, genetic structures that align with historical results and/or earlier results of previous GEs. Thus, the randomization rules may be applied each time the process cycles (in series), or may be applied in parallel to multiple edits that occur at the same time, or both could occur at the same time. Furthermore, the randomization and randomization rules can be created and applied by humans, computers, or other systems.

To create the Base Genetic Structure (109) it requires the combination of a collection of elements including the Randomization of Genetic Structure (107), Existing Genetic Content (108), New Genetic Content (110), and Genetic Content to be Removed (111). It should be noted that the Existing Genetic Content (108), the Base Genetic Structure (109), the New Genetic Content (110), and Genetic Content to be Removed (111) may each be a physical repository (separate or combined) containing GC, or each may be a digital database (separate or combined) storing digital data of GC (or a combination of physical and digital). The Existing Genetic Content (108) may be the primary building blocks of genetic code (gene bases), RNA, DNA, full genomes, entire organisms, populations of organisms, or anything (or portion of thing) in between. In general, this is the GC that is started with to be edited. Based on the information from the randomized genetic structures, New Genetic Content (110) is identified that should be added (and the location of the addition(s) of new GC) to the Existing Genetic Content (108). This additional GC could be as small as a single base element (A, C, G, & T), or as big as an entire genome substitution (or anything in between). Similarly, but generally oppositely, the Genetic Content to be Removed (111) is the GC that should be removed to ensure that the modified GC meets the structure identified in the Randomization of Genetic Structure (107). It may be the case that GC identified to be removed is replaced with new GC to be added, but that is not necessarily the case—the modifications removals (if any) and additions (if any) or moves (if any) may not be replacements. Additionally, as part of this process the GE deals not just with the content of any edit but also the location of any edit. Furthermore, there may be multiple edits being done in an individual modification process and there may be multiple edits occurring in parallel.

After the completion of the final GE, the modified genetic material is allowed to progress to exhibit the results of the edit as part of the Final Structure (112). This may be any of the types of genetic material including but not limited to, just a piece of genetic material, an organism, multiple generations of an organism, a community of the organisms, and/or the broader ecosystem. The results of the genetic edits are reviewed as part of the Evaluation of Results (113). This evaluation process may also take into consideration the various types of experimental error (systematic or random) that may have occurred in the process. This system reviews the results and reports them back to the Genetic Structure Results (103). It should be again noted that the final genetic structure can exist just in the physical world, just in the digital world, or a combination of both. Furthermore, this process of genetic modification and evaluation of the results may be done by a human, a computer, another system, or a combination of these (e.g., user(s)). Additionally, the entire process may run once or several times in full or in part in order to arrive at results that achieve the goal(s) (or do not fully achieve the goal(s)).

Figure 2:
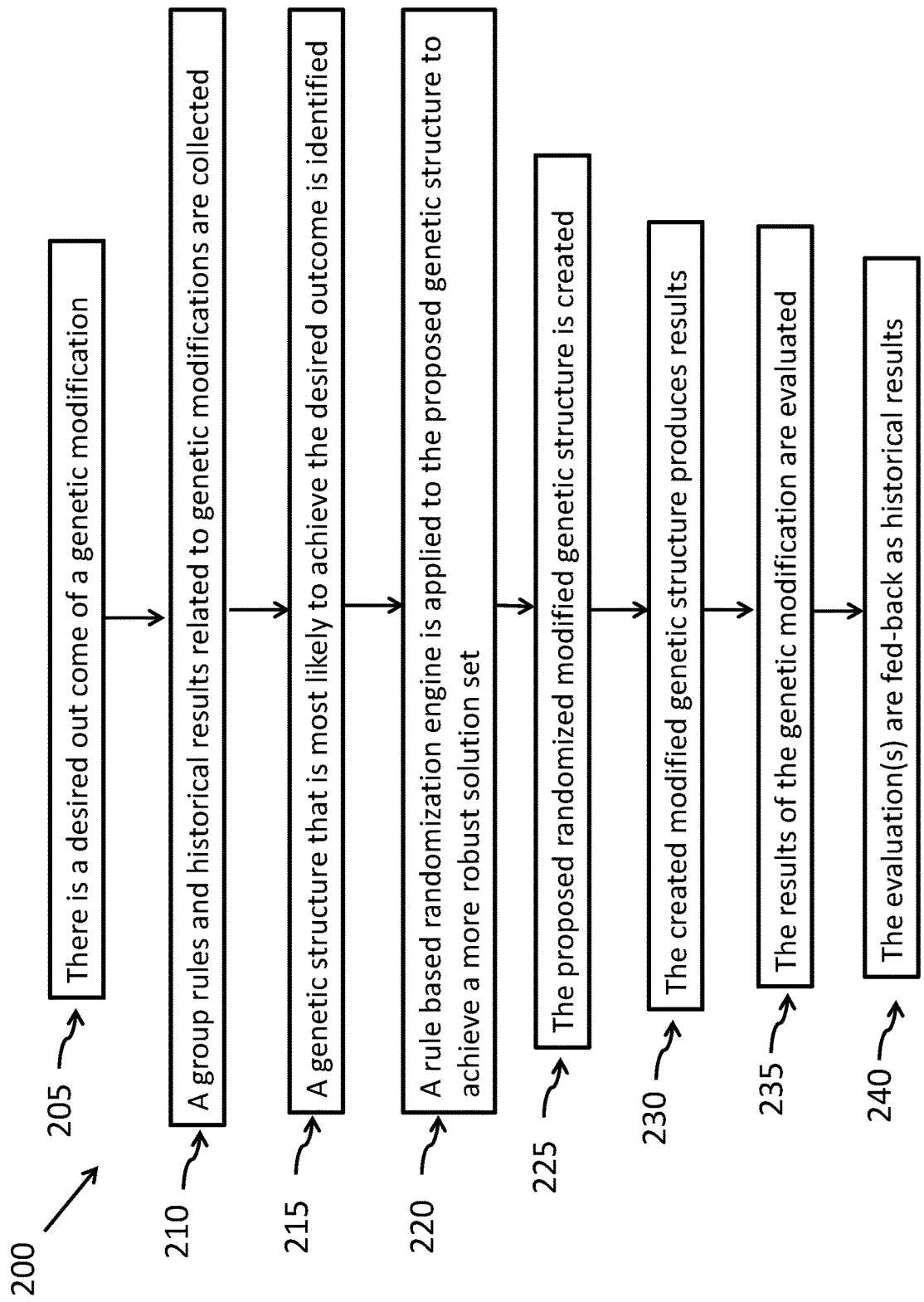
FIG. 2 illustrates a flowchart for a method of creating and evaluating modified genetic content in accordance with an exemplary embodiment.

FIG. 2 illustrates a flowchart for a method according to an exemplary first embodiment. Initially, there is a desired out-come of a genetic modification (205) to genetic content. There can be a wide variety of desired outcomes of genetic modification but there are challenges in achieving the desired outcomes due to the fact that the impact of genetic edits are often not fully understood, there are unanticipated conditions, unintended consequences, and the changes often occur as part of complex interrelated systems. The goal of this process is to take into consideration the unpredictable nature of GEs and produce genetic structure(s) that are more likely to achieve the goal(s) of the genetic modifications.

Once the desired result(s) of a genetic modification is identified a set of rules and historical results related to other prior genetic modifications are collected (210) to help educate and inform the decisions around the current genetic modification in order to facilitate the achievement of the goal(s) or desired results. As described earlier the rules and goal(s) can be broadly defined. The historical results (if any) may be results from earlier cycles of the same process, as well as, historical results from other related genetic modifications (if any) may be used to help to identify a genetic structure that is most likely to achieve the desired outcome (215). This could also be referred to as a "best guess" genetic structure to achieve the goal(s) of the method. But due to the precise nature of genetic editing, if the "best guess" solution is not fully successful it may not just fail to achieve the goal(s) it may also be highly detrimental to the broader environment—a slight mistake in the GE may result in a big miss to the goal(s). At this point a rule-based randomization engine is applied to the proposed genetic structure to achieve a more robust solution set (220). For example, but not limitation, some of the possible randomization techniques that may be used were discussed earlier.

Due to a combination of the highly precise nature of most genetic editing techniques, the unknown impact of many edits, the not fully understood nature of a significant amount of genetic content, the extraordinarily complex environment that surrounds genetic edits, and the fact that the full impact of a given edit may not be fully understood immediately following the edit. A set of one or more alternative edits are identified by applying a rule-based randomization engine to the initial best guess solution to arrive at a stochastic set of genetic edit(s) that may be used to create the set of randomized modified genetic structure(s) (225).

In the exemplary case the randomized modified genetic structure(s) are created by manipulation of genetic material. This may be achieved by any of the genetic editing techniques, or by a combination of multiple editing techniques in series or parallel all at once or over time (even over generations of the genetic material or generations of the organism). This process of editing produces the results (230). These results are then evaluated in comparison to the original goal(s) (235). It should be noted that this editing may be a single specific set of edits done to one set of genetic material or a variety of sets of edits done to multiple sets of genetic material. Again, it should be noted that the edits may occur with actual biological material, digital data, or a combination of the two.

In the example case, these results may be considered successful (achieving the original goal(s)), unsuccessful (not achieving the original goal(s)), mixed (achieving of one or more of the original goal(s) and not achieving one or more of the original goal(s), or having some unintended negative or positive result), or indeterminate (not clearly achieving or failing to achieve the original goal(s) or other result). Please note, that because the edits may be done on multiple sets, the results may be a mix of all of these. Additionally, this evaluation of the results may be done by a human, a computer, another system, or a combination of any of these (e.g., user(s)). These results are fed back (240) into the historical results (210) to help inform any subsequent cycles of the example method. This entire process may be repeated several times completely or in parts. Furthermore, all or some of the steps and or complete cycles may occur in a physical, digital, or mixed manner. Please note, this method does not require any explicit user to initiate, complete, or recycle this process.

Figure 3:
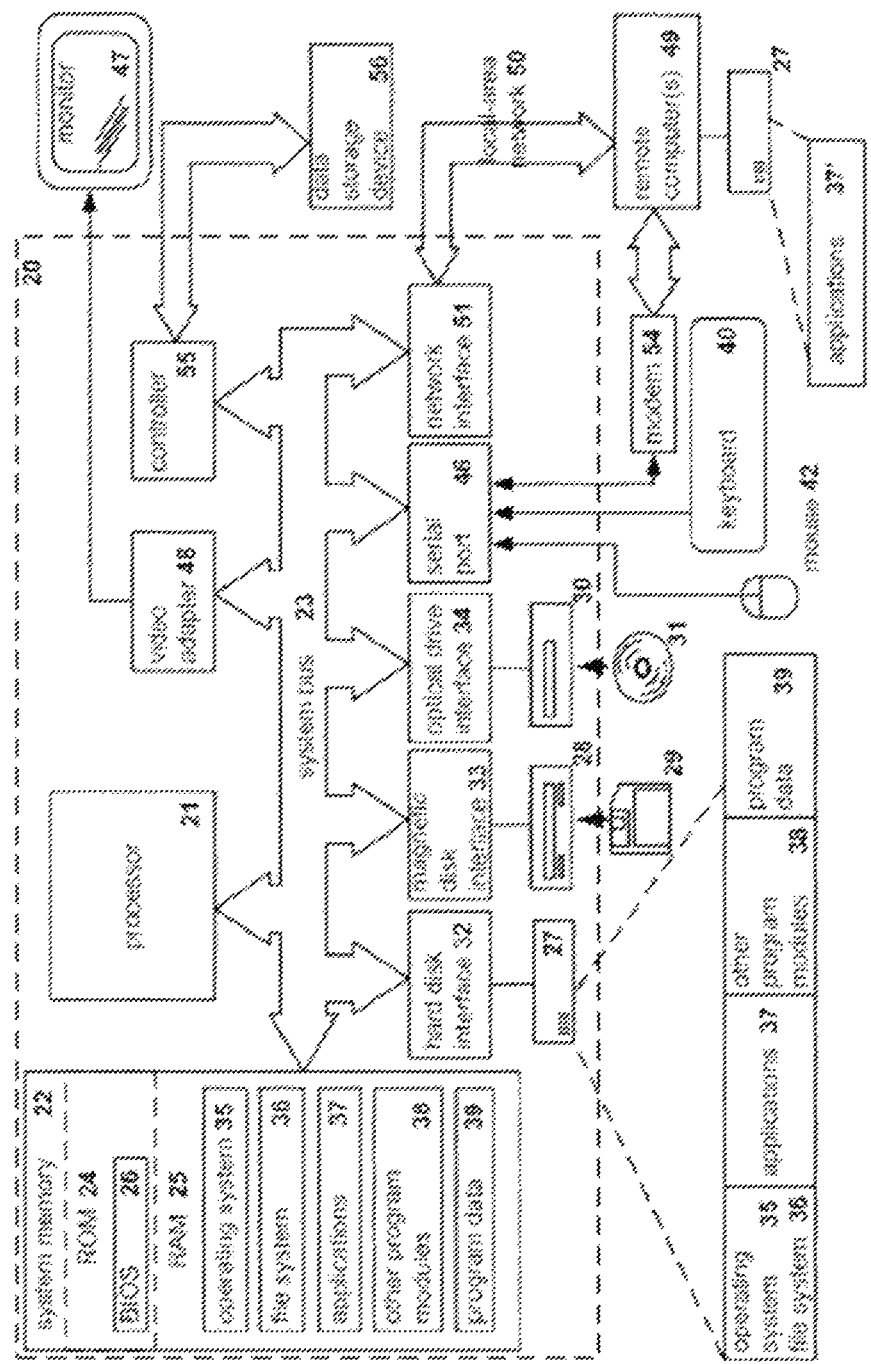
FIG. 3 illustrates an example of a general-purpose computer system in accordance with an exemplary embodiment.

FIG. 3 illustrates an example of a general-purpose (classical or traditional) computer system (which may be a personal computer, a server, or a plurality of personal computers and servers) on which the disclosed system and method can be implemented according to an example aspect. It should be appreciated that the detailed general-purpose computer system can correspond to the GCMS (100) described above with respect to FIG. 1 to implement the algorithms described above. This general-purpose computer system (processor and storage) may exist in a single physical location, with a broadly distributed structure, virtually as a subset of larger computing systems (e.g. in the computing "cloud"), or a combination of any of these. Please note this is provided as an example not a limitation and the example embodiment may also use a quantum computing system in place of the general-purpose computer, or a quantum computer could be used in conjunction with the general-purpose computer. This combination may be performed in parallel, or series, or both, and similarly there may be multiple general-purpose computers or quantum computers used.

As shown, the computer system 20 includes a central processing unit 21, a system memory 22 and a system bus 23 connecting the various system components, including the memory associated with the central processing unit 21. The central processing unit 21 can be provided to execute software code (or modules) for the one or more set of rules discussed above which can be stored and updated on the system memory 22. Additionally, the central processing unit 21 may be capable of executing traditional computing logic, quantum computing, or a combination of both. Furthermore, the system bus 23 is realized like any bus structure known from the prior art, including in turn a bus memory or bus memory controller, a peripheral bus and a local bus, which is able to interact with any other bus architecture. The system memory includes read only memory (ROM) 24 and random-access memory (RAM) 25. The basic input/output system (BIOS) 26 includes the basic procedures ensuring the transfer of information between elements of the personal computer 20, such as those at the time of loading the operating system with the use of the ROM 24.

As noted above, the rules described above can be implemented as modules according to an exemplary aspect. As used herein, the term "module" refers to a real-world device, component, or arrangement of components implemented using hardware, such as by an application specific integrated circuit (ASIC) or field-programmable gate array (FPGA), for example, or as a combination of hardware and software, such as by a microprocessor system and a set of instructions to implement the module's functionality, which (while being executed) transform the microprocessor system into a special-purpose device. A module can also be implemented as a combination of the two, with certain functions facilitated by hardware alone, and other functions facilitated by a combination of hardware and software. In certain implementations, at least a portion, and in some cases, all, of a module can be executed on the processor of a general-purpose computer. Accordingly, each module can be realized in a variety of suitable configurations and should not be limited to any example implementation exemplified herein.

The personal computer 20, in turn, includes a hard disk 27 for reading and writing of data, a magnetic disk drive 28 for reading and writing on removable magnetic disks 29 and an optical drive 30 for reading and writing on removable optical disks 31, such as CD-ROM, DVD-ROM and other optical information media. The hard disk 27, the magnetic disk drive 28, and the optical drive 30 are connected to the system bus 23 across the hard disk interface 32, the magnetic disk interface 33 and the optical drive interface 34, respectively. The drives and the corresponding computer information media are power-independent modules for storage of computer instructions, data structures, program modules and other data of the personal computer 20. Moreover, it is noted that any of the storage mechanisms (including data storage device 56, which may be amongst other things, physical hardware, CDN(s), or the "cloud") can serve as the storage of the media Content, including the Available Content Library (111) described above, according to an exemplary aspect as would be appreciated to one skilled in the art.

The present disclosure provides the implementation of a system that uses a hard disk 27, a removable magnetic disk 29 and/or a removable optical disk 31, but it should be understood that it is possible to employ other types of computer information media 56 which are able to store data in a form readable by a computer (solid state drives, flash memory cards, digital disks, random-access memory (RAM) and so on), which are connected to the system bus 23 via the controller 55.

The computer 20 has a file system 36, where the recorded operating system 35 is kept, and also additional program applications 37, other program modules 38 and program data 39. The user is able to enter commands and information into the personal computer 20 by using input devices (keyboard 40, mouse 42). Other input devices (not shown) can be used: microphone, joystick, game controller, scanner, other computer systems, and so on. Such input devices usually plug into the computer system 20 through a serial port 46, which in turn is connected to the system bus, but they can be connected in other ways, for example, with the aid of a parallel port, a game port, a universal serial bus (USB), a wired network connection, or wireless data transfer protocol. A monitor 47 or other type of display device is also connected to the system bus 23 across an interface, such as a video adapter 48. In addition to the monitor 47, the personal computer can be equipped with other peripheral output devices (not shown), such as loudspeakers, a printer, and so on.

The personal computer 20 is able to operate within a network environment, using a network connection to one or more remote computers 49, which can correspond to the remote viewing devices, i.e., the IP connected device (e.g., a smartphone, tablet, personal computer, laptop, media display device, or the like). Other devices can also be present in the computer network, such as routers, network stations, peer devices or other network nodes.

Network connections 50 can form a local-area computer network (LAN), such as a wired and/or wireless network, and a wide-area computer network (WAN). Such networks are used in corporate computer networks and internal company networks, and they generally have access to the Internet. In LAN or WAN networks, the personal computer 20 is connected to the network 50 across a network adapter or network interface 51. When networks are used, the personal computer 20 can employ a modem 54 or other modules for providing communications with a wide-area computer network such as the Internet or the cloud. The modem 54, which is an internal or external device, is connected to the system bus 23 by a serial port 46. It should be noted that the network connections are only examples and need not depict the exact configuration of the network, i.e., in reality there are other ways of establishing a connection of one computer to another by technical communication modules, such as Bluetooth.

In various aspects, the systems and methods described herein may be implemented in hardware, software, firmware, or any combination thereof. If implemented in software, the methods may be stored as one or more instructions or code on a non-transitory computer-readable medium. Computer-readable medium includes data storage. By way of example, and not limitation, such computer-readable medium can comprise RAM, ROM, EEPROM, CD-ROM, Flash memory or other types of electric, magnetic, or optical storage medium, or any other medium that can be used to carry or store desired program code in the form of instructions or data structures and that can be accessed by a processor of a general purpose computer.

In the interest of clarity, not all of the routine features of the aspects are disclosed herein. It will be appreciated that in the development of any actual implementation of the present disclosure, numerous implementation-specific decisions must be made in order to achieve the developer's specific goal(s), and that these specific goal(s) will vary for different implementations and different developers. It will be appreciated that such a development effort might be complex and time-consuming but would nevertheless be a routine undertaking of engineering for those of ordinary skill in the art having the benefit of this disclosure.

Furthermore, it is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of the skilled in the relevant art(s). Moreover, it is not intended for any term in the specification or claims to be ascribed an uncommon or special meaning unless explicitly set forth as such.

The various aspects disclosed herein encompass present and future known equivalents to the known modules referred to herein by way of illustration. Moreover, while aspects and applications have been shown and described, it would be apparent to those skilled in the art having the benefit of this disclosure that many more modifications than mentioned above are possible without departing from the inventive concepts disclosed herein.

What is claimed is:

1. A system for selecting and editing exiting genetic content in order to achieve a set of goals while minimizing resource consumption, the system comprising:
    at least one electronic database configured to store at least one set of existing genetic content configured to be edited by means of the addition of at least one set of new genetic content stored in at least one electronic database or the removal of at least one set of genetic content, the identity of which is stored in at least one electronic database;
    at least one processor with software instructions stored thereon that, when executed by the at least one processor, configure the at least one processor to execute:
    a base genetic structure rules engine configured to generate at least one approved genetic structure characteristic based at least on one ecosystem rule;
    a predictive rules engine configured to generate at least one genetic structure characteristic based on at least one other historical genetic editing result,
    a genetic structure rules engine configured to generate a set of approved genetic structures including a best guess genetic structure and at least one second best guess genetic structure,
    a randomization rules engine to randomly select a genetic structure from the set of approved genetic structures,
    a base genetic structure engine configured to generate a set of selected edited genetic content by
    adding at least one set of new genetic content to the at least one set of existing genetic content, or
    removing at least one set of existing genetic content from the at least one set of existing genetic content, and
    at least one processor configured to enable the edited genetic content to exhibit the results of the editing;
    wherein the results of the editing are evaluated as to their relative achievement of the ecosystem rules and goals;
    wherein at least one predictive rules engine is further configured to
receive updates related to at least one other historical result and at least one edited genetic structure result.

2. The system according to claim 1, wherein the genetic structure rule set engine is further configured to calculate the set of approved genetic structures based on at least one other historical result of genetic editing.

3. A method for selecting and editing exiting genetic content in order to achieve a set of goals while minimizing resource consumption, the method comprising:
    storing in at least one electronic database configured to store at least one set of existing genetic content configured to be edited by means of the addition of at least one set of new genetic content stored in at least one electronic database or the removal of at least one set of genetic content, the identity of which is stored in at least one electronic database;
    generating by at least one processor with software instructions stored thereon that, when executed by the at least one processor, configure the at least one processor to execute:
    generating by at least one base genetic structure rules engine configured to generate at least one approved genetic structure characteristic based at least on one ecosystem rule;
    applying a predictive rules engine configured to generate at least one genetic structure characteristic based on at least one other historical genetic editing result,
    generating a set of approved genetic structures including a best guess genetic structure and at least one second best guess genetic structure,
    applying a randomization engine to the set of approved genetic structures to select a genetic structure,
    applying a base genetic structure engine configured to generate a set of selected edited genetic content by
    adding at least one set of new genetic content to the at least one set of existing genetic content, or
    removing at least one set of existing genetic content from the at least one set of existing genetic content, and
    utilizing at least one processor configured to enable the edited genetic content to exhibit the results of the editing;
    wherein the results of the editing are evaluated as to their relative achievement of the ecosystem rules and goals;
    wherein at least one predictive rules engine is further configured to:
receive updates related to at least one other historical result and at least one edited genetic structure result.

4. The method according to claim 3, wherein the genetic structure rule set engine is further configured to generate the set of approved genetic structures based on at least one other historical result of genetic editing.

* * * * *